United States Patent [19]
Günther-Hanssen

[11] Patent Number: 5,994,585
[45] Date of Patent: Nov. 30, 1999

[54] AMINATION PROCESS

[75] Inventor: Johan Günther-Hanssen, Mölndal, Sweden

[73] Assignee: Akzo Nobel N.V., Arnhem, Netherlands

[21] Appl. No.: 09/190,486

[22] Filed: Nov. 12, 1998

[30] Foreign Application Priority Data

Nov. 11, 1997 [SE] Sweden .................................. 9704116

[51] Int. Cl.$^6$ ................................................. C07C 209/00
[52] U.S. Cl. ......................... 564/480; 564/475; 564/477; 564/479; 564/511; 564/512
[58] Field of Search ..................... 564/475, 477, 564/479, 480, 511, 512

[56] References Cited

U.S. PATENT DOCUMENTS

| | | | |
|---|---|---|---|
| 2,365,721 | 12/1944 | Olln et al. | 260/585 |
| 3,723,529 | 3/1973 | Pitts et al. | 260/583 |
| 3,766,184 | 10/1973 | Johansson et al. | 260/268 |
| 4,123,462 | 10/1978 | Best | 260/585 |
| 4,347,381 | 8/1982 | Tuvell | 564/2 |
| 4,404,405 | 9/1983 | Winters | 564/482 |
| 4,977,266 | 12/1990 | Burgess et al. | 544/398 |

FOREIGN PATENT DOCUMENTS

| | | | |
|---|---|---|---|
| 0 146 508 | 6/1985 | European Pat. Off. | B01J 23/89 |
| 0 254 335 | 1/1988 | European Pat. Off. | B01J 27/128 |
| 0 262 562 | 4/1988 | European Pat. Off. | C07C 85/26 |
| 0 729 785 | 9/1996 | European Pat. Off. | B01J 23/46 |
| 0 737 669 | 10/1996 | European Pat. Off. | C07C 213/02 |

*Primary Examiner*—Samuel Barts
*Attorney, Agent, or Firm*—Ralph J. Mancini

[57] ABSTRACT

The present invention relates to an amination process for the manufacture of polyamines. The purpose of the process is to increase the selectivity of linear aminated products and to prevent the formation of discoloring by-products or by-products which may later cause discoloration. According to the process this is achieved by performing, in a first part of the process, the amination to a conversion degree of between 50 and 98% by weight, calculated on the total yield of polyamines, at a proportionally time-weighted average temperature, which is at least 15° C. higher than the proportionally time-weighted average temperature in the remaining part.

10 Claims, No Drawings

AMINATION PROCESS

FIELD OF THE INVENTION

The present invention relates to an amination process for the manufacture of polyamines. The process is performed under specific temperature conditions which lead to an increase in selectivity for linear polyamines and a reduction in colour.

BACKGROUND OF THE INVENTION

Desirable objectives of an amination process are to increase the amount of linear amination products and decrease the formation of cyclic amination products. See for example the U.S. Pat. Nos. 2,365,721 and 3,766,184 and EP-A-146 508, EP-A-254 335, EP-A-729 785 and EP-A-737 669.

Another desired objective of an amination process is to reduce the amounts of by-products which may cause discolouration of the polyamines themselves or, at a later stage, cause discolouration when the polyamines are used as intermediates or in compositions. A number of methods for reducing the colour has been suggested. For example, the U.S. Pat. No. 3,723,529 suggests treatment with activated carbon and the U.S. Pat. No. 4,347,381, treatment with a bleaching agent. EP-A-262 562 discloses a method for the reduction in the colour by contacting the coloured polyamines at elevated temperature and pressure with a catalytically effective amount of a hydrogenation catalyst in the presence of a hydrogen containing atmosphere. However, although all of these methods do result in a reduction in colour the post-treatment is costly and does not prevent the occurrence of discolouration.

The purpose of the present invention is to increase the selectivity of the linear aminated products and at the same time prevent the formation of discolouring by-products or by-products which later may be the future sources of discolouration, for example when neutralizing the aminated products with an acid. Furthermore, the solution to the above-mentioned challenges should be uncomplicated and should not lead to other problems.

SUMMARY OF THE INVENTION

The present invention generally relates to an amination process for the manufacture of polyamines in the presence of a catalytically effective amount of a dehydrogenation/hydrogenation catalyst. The process is characterized in, that the amination is, in a first part of the process, performed to a conversion degree of 50–98% by weight, calculated on the total yield of polyamines, at a proportionally time-weighted average temperature, which is at least 15° C. higher than the proportionally time-weighted average temperature during the reaction time in the remaining part.

BACKGROUND OF THE INVENTION

Surprisingly, it has been found that the above-mentioned objectives can be achieved by performing the amination process for the manufacture of polyamines under specific temperature conditions. More specifically the amination is, in a first part of the process, performed to a conversion degree of between 50 and 98% by weight, preferably 55 to 95% by weight, calculated on the total yield of polyamines at a proportionally time-weighted average temperature, which is at least 15° C., preferably between 25° C. and 100° C. and most preferably, 35° C. to 70° C. higher than the proportionally time-weighted average temperature in the remaining part. In this context the expression "time-weighted average temperature" is an average temperature where the reaction time is proportionally taken into consideration.

By the process of the invention the amount of linear aminated products such as ethylenediamine, diethylenetriamine, triethylenetetraamine and aminoethylethanolamine, is increased while the amount of cyclic compounds is lowered. At the same time an essential reduction in discolouration is achieved. The process may be carried out in one reactor equipped with a temperature control device to fulfil the above conditions or it may be performed in at least two separate reactors with separate temperature controls. Normally the catalyst is the same throughout the entire reaction zone or zones, but it is also possible to have different dehydrogenation/hydrogenation catalysts in the reaction zone or zones, e.g. catalysts with different selectivities. The average temperature during the first part of the reaction may be between 160° C. and 300° C., preferably between 170° C. and 230° C., and in the remaining part, 100° C. to 190° C., preferably between 110° C. and 180° C.

The amination reaction of the present invention includes the amination of alcohols, phenols, diols, alkanolamines and alkylene oxides with ammonia or primary or secondary amines. The aminated compounds should preferably be di-functional. All hydrogen atoms attached to an amino group are potentially replaceable by the alkyl radical of the reacting alkylene oxide, hydroxyl or carbonyl compound, so the reaction product will therefore be a mixture of primary, secondary, and tertiary amines. When aminating compounds such as ethylene glycols and ethanolamines, not only straight chain di- and polyamines but also branched di- and polyamines and six membered heterocyclic amines, such as piperazine, morpholine, and their derivatives, are obtained.

The most desirable products in the manufacture of ethylene amines are those products which mainly contain primary and secondary amino groups. Amination products containing tertiary amino groups and heterocyclic rings are generally of less commercial value. The present process, surprisingly, increases the selectivity for the formation of primary, secondary and non-cyclic compounds.

Alkylene oxides suitable for amination are those having 2–22 carbon atoms in the alkylene group. Specific examples are ethylene oxide, 1,2-propylene oxide, 1,2-butylene oxide and 2,3-butylene oxide. Aliphatic alcohols which can be aminated in the process of the present invention, include saturated aliphatic monohydric and polyhydric alcohols of 1 to 30 carbon atoms. Examples of saturated monohydric alcohols are methanol, ethanol, propanol, isopropanol, n-butanol, sec-butanol, tert-butanol, isobutanol, n-pentanol, isopentanol, neopentanol, n-hexanol, isohexanol, 2-ethyl hexanol, cyclohexanol, n-heptanol, n-octanol, 2-octanol, isooctanol, and tert-octanol, and various isomers of nonanol, decanol, undecanol, dodecanol, tridecanol, tetradecanol, hexadecanol, and octadecanol and arachidyl alcohol. Examples of aliphatic dihydric alcohols of 2 to 30 carbon atoms include ethylene glycol, diethylene glycol, triethylene glycol, tetraethylene glycol, and higher polyethylene glycols, 1,2- and 1,3-propylene glycol, dipropylene glycol, tripropylene glycol and higher polypropylene glycols, 1,2-butylene glycol, 1,3-butylene glycol, 1,4-butylene glycol, 2,3-butylene glycol, dibutylene glycol, tributylene glycol or higher polybutylene glycols, isomers of pentanediol, hexanediol, octanediol, nonanediol, decanediol, undecanediol, dodecanediol and tridecanediol; tetradecanediol, pentadecanediol, hexadecanediol, octadecanediol, eicosanediol. Examples of trihydric and higher polyols of 3 to 30 carbon atoms include glycerol, erythritol, pentaerythritol, sorbitol, mannitol, trimethylol ethane, trimethylol propane, heptanetriol, and decanetriol.

Phenol compounds suitable for amination include phenol, o-cresol, m-cresol, p-cresol, pyrocatechin, resorcinol, hydroquinone and isomers of xylenol. Suitable aliphatic aminoalcohols are those having from 2 to 30 carbon atoms, such as monoethanolamine, diethanolamine, aminoethyl ethanolamine, propanolamines, butanolamines, pentanolamines, hexanolamines, heptanolamines, octanolamines, decanolamines, dodecanolamines, tetradecanolamines, hexadecanolamines, octadecanolamines, and eicosanolamines. In addition, mixtures of any of the above-mentioned compounds containing hydroxyl can be employed, for examples, mixtures of ethylene glycol and monoethanolamine, or mixtures of alkanolamines which are obtained by a reaction between alkylene oxides and ammonia.

The aminating agents are either ammonia, primary amines or secondary amines. The amines generally have either alkyl groups of 1–20 carbon atoms, cycloalkyl groups of 5–8 carbon atoms and aryl or arylalkyl groups of 6–40 carbon atoms or mixtures thereof. Examples of suitable amines are methylamine, ethylamine, n-butylamine, isobutylamine, ethylenediamine, benzylamine, dimethylamine and diethylamine. The aminating agents can be used individually or in combinations.

The dehydrogenation/hydrogenation catalyst to be used in the process of this invention can be any conventional amination catalyst. Usually the catalyst contains, as the catalytically active part, at least one metal selected from the group consisting of nickel, chromium, cobalt, copper, ruthenium, iron, calcium, magnesium, strontium, lithium, sodium, potassium, barium, cesium, tungsten, silver, zinc, uranium, titanium, rhodium, palladium, platinum, iridium, osmium, gold, molybdenum, rhenium, cadmium, lead, rubidium, boron and manganese or mixtures thereof. The metalic part of the catalyst should contain at least 70% by weight, preferably above 80% by weight, of nickel, chromium, cobalt, copper, palladium, ruthenium or iron or mixtures thereof, which has the main responsibility for the dehydrogenation/hydrogenation catalytic effect. The catalytic effects are often promoted to achieve, e.g. improved selectivity for desired products, by the presence of minor amounts of other metals, such as those selected from the group consisting of calcium, magnesium, strontium, lithium, sodium, potassium, barium, cesium, tungsten, iron, ruthenium, zinc, uranium, titanium, rhodium, palladium, platinum, iridium, osmium, silver, gold, molybdenum, rhenium, cadmium, lead, rubidium, boron and manganese. These promoters normally constitute from 0.1 to 30%, preferably from 1 to 20% by weight, of the total amount of the catalytic metals. The catalytic metals are normally supported by a porous metal oxide carrier although other types of carriers, such as carbon, may also be utilized. Examples of suitable support materials are various forms of alumina, silica, kieselguhrs, alumina-silica, alumina-titania, alumina-magnesia and alumina-zirconia. The carrier normally constitutes between 50 and 97% by weight of the whole catalyst. In a preferred embodiment the catalyst is a metallic catalyst containing nickel and promoted with ruthenium, rhenium, palladium or platinum or mixtures thereof in metallic form on a porous metal oxide support containing alumina. The amount of the catalyst is not crucial, but normally it is 0.1–25%, preferably 1–15% by weight of the total amount of starting reactants in a batchwise process. Dehydrogenation/hydrogenation catalysts as described above are to be found for example in EP-A-146 508, EP-A-729 785, EP-A-737 669, U.S. Pat. No. 2,365,721 and U.S. Pat. No. 4,123,462.

The reaction between the aminating agent and the compound to be aminated is best carried out in the presence of hydrogen gas, so as to inhibit or reduce the poisoning of the catalyst and to ensure a high yield of the desired aliphatic amine products. Generally, the quantity of hydrogen gas required is relatively small, and corresponds to a ratio of from about 0.1 to about 2 moles per mole of the compound to be aminated. Higher quantities of hydrogen can be applied, but generally, however, without any obvious beneficial effect. The aminating agent, such as ammonia, should be present in excess in the mixture, for example, a ratio of 2 to 30 moles aminating agent per mole of compound to be aminated, but preferably within the range of from 5 to about 15 moles per mole of compound to be aminated.

The amination process is carried out at a relatively high pressure. The pressure applied is dependent upon the molar ratio of the reactants, the reaction temperature, the amount of hydrogen, and the type of operation. Generally, the pressure should be high enough to keep most of the reactants in the liquid phase. The pressure is normally within the range of 8 to 40 Mpa and preferably between 15 and 30 Mpa.

The invention is further illustrated by the following Examples.

EXAMPLE 1

An amination process was performed by continuously reacting monoethanolamine and ammonia in a weight ratio of 1 to 4 in the presence of a dehydrogenation/hydrogenation catalyst and hydrogen in a first reaction step. The catalyst comprised of 10% by weight of nickel and 0.75% by weight of ruthenium on an activated alumina support in accordance with EP Patent No. 254 335. The reaction temperature in the first reaction step was 200° C. and the conversion of monoethanolamine to an aminated product was 55% by weight. In the subsequent reaction step the reaction temperature was lowered to 170° C. and the reaction was continued in batch modes to a conversion of monoethanolamine to 75% by weight in the presence of the same dehydrogenation/hydrogenation catalyst as in the first step. This means that about 73% by weight of the conversion took place in the first reaction step.

As a control test the same reaction as above was performed in two steps to a conversion of 75% of monoethanolamine, but with the exception that the temperature in the second step was also 200° C. The reaction products were analyzed with respect to the amount of ethylenediamine (EDA), piperazine (PIP), diethylenetetraamine (DETA), aminoethylethanolamine (AEEA) and of the total amount of piperazine compounds.

Ammonia and hydrogen were removed from the reaction mixtures, which were then diluted with water at a weight ratio of 1:1. After the addition of hydrochloric acid to pH 3.5, the discolouration was measured according to Hazen.

The following results were obtained.

TABLE 1

| Process | Amount % by weight | | | | | Colour |
| | EDA | PIP | DETA | AEEA | Tot PIP | Hazen |
| --- | --- | --- | --- | --- | --- | --- |
| Invention | 46.7 | 17.2 | 15.5 | 10.3 | 20.4 | 150 |
| Control | 52.6 | 19.9 | 11.6 | 7.8 | 23.1 | 320 |

From the result it is evident that the formation of cyclic piperazine compounds was reduced by about 12% by weight in the amination process of the invention when compared with the control. In addition a considerable reduction in colour was obtained.

EXAMPLE 2

Amination reactions were performed in the same manner as in Example 1. However, the catalysts used in the second step contained 15% by weight of metallic nickel or 15% by weight of metallic nickel, which were in some cases promoted with 0.75% by weight of ruthenium, palladium, rhenium or platinum. Control tests were also performed with the temperature again being maintained at 200° C. in the second step.

After the reactions the contents and discolouration of the amination mixtures obtained were determined in the same manner as in Example 1.

The following results were obtained.

| Test | Promoter | Amount, % by weight | | | | | Colour |
| | | EDA | PIP | DETA | AEEA | Tot PIP | Hazen |
| --- | --- | --- | --- | --- | --- | --- | --- |
| 1 | — | 51.5 | 16.5 | 14.7 | 8.2 | 19.3 | 52 |
| 2 | Ru | 52.3 | 16.7 | 14.5 | 7.8 | 19.5 | 58 |
| 3 | Re | 52.7 | 20.2 | 12.6 | 6.9 | 23.4 | 76 |
| 4 | Pt | 46.8 | 17.7 | 15.2 | 8.7 | 21.2 | 132 |
| 5 | Pd | 44.2 | 19.3 | 16.0 | 8.4 | 23.1 | 32 |
| A | — | 49.7 | 23.2 | 11.1 | 5.5 | 28.8 | 68 |
| B | Ru | 53.4 | 17.7 | 13.0 | 7.3 | 21.1 | 120 |
| C | Re | 51.1 | 23.0 | 10.2 | 6.5 | 27.7 | 128 |
| D | Pt | 50.8 | 19.9 | 12.5 | 7.1 | 23.6 | 350 |
| E | Pd | 49.0 | 20.8 | 12.5 | 7.1 | 24.9 | 60 |

From the results, it is evident that both the total amount of piperazine compounds and the colour are reduced when the process is performed in accordance with the invention, tests 1–5, as compared with the control, tests A–E.

I claim:

1. An amination process for the manufacture of polyamines in the presence of a catalytically effective amount of a dehydrogenation/hydrogenation catalyst, wherein the amination is, in a first part of the process, performed to a conversion degree of 50–98% by weight, calculated on the total yield of polyamines, at a proportionally time-weighted average temperature, which is at least 15° C. higher than the proportionally time-weighted average temperature during the reaction time in the remaining part.

2. Process in accordance with claim 1, wherein the temperature in the first part is between 25° C. and 100° C. higher than the temperature in the remaining part.

3. The process of claim 1 wherein the temperature in the first part of the process is between 160° C. and 300° C. and that the temperature in the remaining part is between 100° C. and 190° C.

4. The process of claim 1 wherein the polyamines are obtained by aminating a member from the group consisting of alcohols, phenols, diols, alkanolamines and alkylene oxides with ammonia or primary amines or secondary amines.

5. The process of claim 4 wherein monoethanolamine is aminated with ammonia.

6. The process of claim 1 wherein the dehydrogenation/hydrogenation catalyst contains, as the catalytically active part, at least one metal selected from the group consisting of nickel, chromium, cobalt, copper, ruthenium, iron, calcium, magnesium, strontium, lithium, sodium, potassium, barium, cesium, tungsten, ruthenium, zinc, uranium, titanium, rhodium, palladium, platinum, iridium, osmium, silver, gold, molybdenum, rhenium, cadmium, lead, rubidium, boron, manganese and mixtures thereof.

7. The process of claim 6 wherein the catalytically active part of the catalyst contains at least 70% by weight of metals selected from the group consisting of nickel, chromium, cobalt, copper, palladium, ruthenium, iron and mixtures thereof.

8. The process of claim 7 wherein the catalyst is promoted with metals selected from the group consisting of calcium, magnesium, strontium, lithium, sodium, potassium, barium, cesium, tungsten, iron, ruthenium, zinc, uranium, titanium, rhodium, palladium, platinum, iridium, osmium, silver, gold, molybdenum, rhenium, cadmium, lead, rubidium, boron and manganese, in an amount from 1–20% by weight of the total amount of metallic metals.

9. The process of claim 6 wherein the metals are supported on a carrier of metal oxide.

10. The process of claim 6 wherein the catalyst contains a metallic nickel promoted with ruthenium, rhenium, palladium or platinum or mixtures thereof on a porous metal oxide support containing alumina.

* * * * *